United States Patent [19]
Nair et al.

[11] Patent Number: 5,908,929
[45] Date of Patent: Jun. 1, 1999

[54] PROCESS FOR THE MANUFACTURE OF THE ANTIBIOTIC 7-(D-α-AMINO-α-PHENYLACETAMIDO)-3-METHYL-3-CEPHEM-4-CARBOXYLIC ACID (CEPHALEXIN) AND PHARMACEUTICALLY ACCEPTABLE SALTS THEREOF

[75] Inventors: Vellate Ravindranathan Nair; Anil Shankar Chowdhary; Jyoti Rajesh Agrawal, all of Gujarat, India

[73] Assignee: Vitara Chemicals Limited, Maharashtra, India

[21] Appl. No.: 08/890,107

[22] Filed: Jul. 9, 1997

[30]  Foreign Application Priority Data

Dec. 5, 1996 [IN] India ............................. 586/96

[51] Int. Cl.$^6$ .................. C07D 499/12; C07C 229/36
[52] U.S. Cl. ............................................. 540/230
[58] Field of Search ............................... 540/230

[56]  References Cited

U.S. PATENT DOCUMENTS

| | | | |
|---|---|---|---|
| 3,507,861 | 4/1970 | Morin et al. | 260/243 |
| 3,518,260 | 6/1970 | Spencer et al. | 260/243 |
| 3,634,416 | 1/1972 | Schofield | 260/243 |
| 3,671,449 | 6/1972 | Jackson | 260/243 |
| 3,676,437 | 7/1972 | Siddons | 260/243 |
| 3,694,437 | 9/1972 | Jackson | 240/243 |
| 3,864,340 | 2/1975 | Ishimaru et al. | 260/243 |
| 4,299,955 | 11/1981 | Falciani et al. | 544/30 |

FOREIGN PATENT DOCUMENTS

| | | |
|---|---|---|
| 0 127 541 A2 B1 | 12/1984 | European Pat. Off. . |
| 552162 | 2/1986 | Spain . |
| 2240102 | 7/1991 | United Kingdom . |

*Primary Examiner*—Mark L. Berch
*Attorney, Agent, or Firm*—Ladas & Parry

[57]  ABSTRACT

A process for the manufacture of the antibiotic 7-(D-α-amino-α-phenylacetamido)-3-methyl-3-cephem-4-carboxylic acid (cephalexin) and pharmaceutically acceptable salts thereof. It consists of reacting an enamine protected potassium salt of D-(−)-α-phenyl glycine (Dane salt) with an acid chloride in a twin solvent mixture in the presence of a pyridine derived twin catalytic mixture at −20 to −65° C. The resulting mixed anhydride is condensed with an alkyl guanidinium salt solution of 7-amino desacetoxy cephalosporanic acid (7-ADCA) at −10° C. to −65° C. followed by hydrolytic cleavage of the enamine derivative of the resulting compound with an aqueous mineral acid and precipitation of the antibiotic in the presence of an alcohol as co-solvent. If desired the cephalexin is converted into its pharmaceutically acceptable salts in a known manner.

22 Claims, No Drawings

PROCESS FOR THE MANUFACTURE OF THE ANTIBIOTIC 7-(D-α-AMINO-α-PHENYLACETAMIDO)-3-METHYL-3-CEPHEM-4-CARBOXYLIC ACID (CEPHALEXIN) AND PHARMACEUTICALLY ACCEPTABLE SALTS THEREOF

BACKGROUND OF THE INVENTION

This invention relates to a process for the manufacture of the antibiotic 7-(D-α-amino-α-phenyl acetamido)-3-methyl-3-cephem-4-carboxylic acid (cephalexin) of the formula 1:

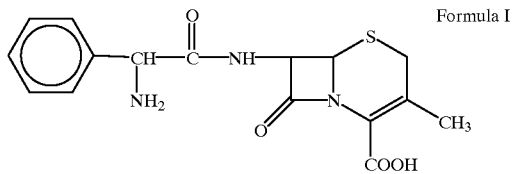

Formula I and pharmaceutically acceptable salts thereof.

The antibiotic of the formula 1 is well known as perorally active antibacterial having broad spectrum activity. Several processes for the manufacture of the compound of the formula 1 are reported.

U.S. Pat. Nos. 3,507,861, 3,671,449, 3,634,416 and 3,676,437 relate to the manufacture of compound of the formula 1 by esterification of 7-amino Desacetoxy Cephalosporanic Acid (7-ADCA) of the formula 2:

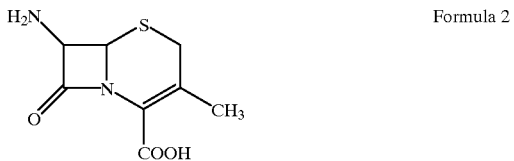

Formula 2 with reagents containing ester groups such as 2,2,2-trichloromethyl, p-nitrobenzyl or trlmethyl silyl to obtain ester protected 7-ADCA derivative ot the formula 3:

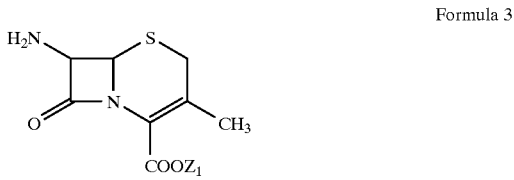

Formula 3 wherein $Z_1$ is ester group such as 2,2,2-trichloromethyl, p-nitrobenzyl or trimethysilyl followed by condeneation with a mixed anhydride of the formula 4:

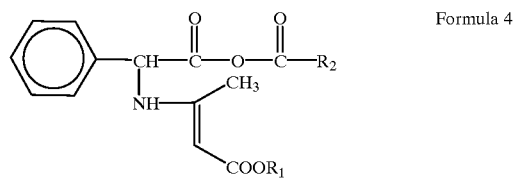

Formula 4 wherein $R_1$ is methyl or ethyl and R2 is ethyl or tertiary butyl obtained by reacting D-(−)-α phenyl glycine derivative (Dane salt) of the formula 5:

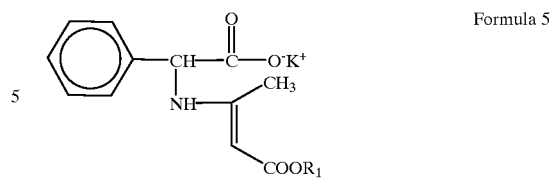

Formula 5 wherein $R_1$ is as defined above with an acid chloride of the formula $R_2$—COCl, wherein $R_2$ is as defined above. The resulting compound of the formula 6a:

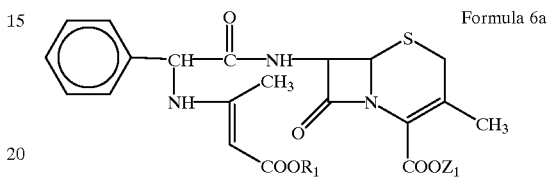

Formula 6a wherein $R_1$ and $Z_1$ are as defined above is hydrolysed with an aqueous mineral acid to cleave the ester group and obtain the compound of the formula 1. The procedures for isolation and purification of the compound of the formula 1 from the reaction mixture are complicated and difficult due to the ester functionality. Therefore, these processes are difficult and inconvenient to carry out. Besides these processes give the compound of the formula 1 in low yield (50%) and low purity and are not economical and commercially viable.

U.S. Pat. No. 3,518,260 relates to the manufacture of compound of the formula 1 by dissolving 7-ADCA of the formula 2 in water and subsequently condensing with mixed anhydride of the formula 4 obtained by reacting Dane salt of the formula 5 with an acid chloride of the formula $R_2$—COCl in acetone. The resulting compound of the formula 6b:

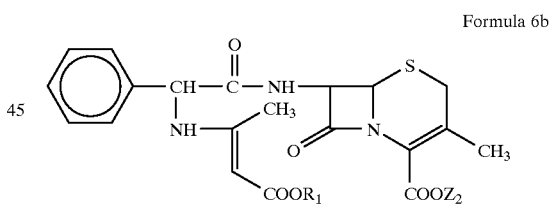

Formula 6b wherein $R_1$ is as defined above and $Z_2$ is an alkyl amine such as triethyl amine is hydrolyzed with an aqueous mineral acid to cleave the enamine protected group and give the compound of the formula 1. This process suffers from dismal yields as low as 25 to 40% of the compound of the formula 1 and is not economical and commercially viable. Besides, separation and purification of compound of the formula 1 from the reaction mixture is difficult and complicated due to the presence of acetone in the reaction mixture. Therefore, it is very difficult and inconvenient to carry out the process.

U.S. Pat. No. 3,694,437 relates to the manufacture of compound of the formula 1 by conversion of Dane salt of the formula 5 to mixed anhydride of the formula 4 and condensing with silyl derivatives of 7-ADCA of the formula 2 obtained by silylation of 7-ADCA of the formula 2. The resulting compound of the formula 6c:

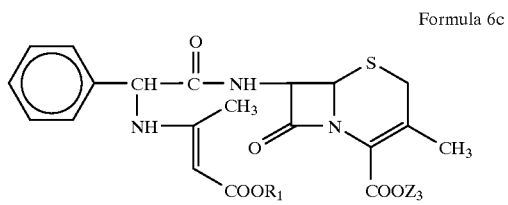

Formula 6c wherein $R_1$ is as defined above and $Z_3$ is trimethyl silyl group is hydrolysed with an aqueous mineral acid to cleave the silyl group and give the compound of the formula 1. This process also suffers from poor yields (50%) and low purity of compound of the formula 1 and is, therefore, uneconomical and commercially not viable.

U.S. Pat. No. 3,864,340 relates to the manufacture of compound of the formula 1 by reacting 7-ADCA of the formula 2 with triethlyl amine using alcohol in very large excess (ca 26 volumes) as solvent followed by condensation with a mixed anhydride of the formula 4 prepared from an enamine protected Dane salt of the formula 5. The resulting compound of the formula 6d:

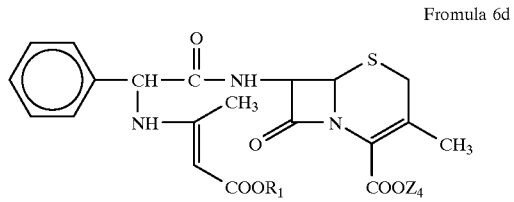

Fromula 6d wherein $R_1$ is as defined above and $Z_4$ is triethyl amine is hydrolyzed with an aqueous mineral acid to remove the triethyl amine group and give compound of the formula 1. The process gives the compound of the formula 1 in very low yields (c.a 35–40%) and low purity and is therefore, uneconomical and commercially not viable. Separation and purification of compound of the formula 1 from the reaction mixture is difficult and cumbersome due to the alcohol emulsion. Therefore, it is difficult and inconvenient to carry out the process.

U.S. Pat. No. 4,299,955 relates to the manufacture of compound of the formula 1 by reacting a mixed anhydride of the formula 4 prepared from Dane salt of the formula 5 with avoid chloride of the formula $R_2COCl$ in acetone with an aqueous alkyl amine solution of 7-ADCA of the formula 2 and a solvent such as dimethyl sulfoxide, dimethyl acetamide, formamide or dimethyl formamide. The resulting compound of the formula 6e:

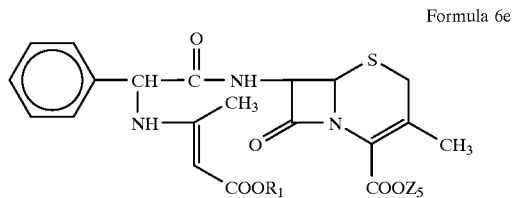

Formula 6e wherein $R_1$ is as defined above and $Z_5$ is triethyl amine is hydrolyzed with an aqueous mineral acid to remove the alkyl group and obtain compound of the formula 1. This process is difficult and inconvenient to carry out due to the separation and purification of compound of the formula 1 from the acetone emulsion is difficult and inconvenient. Also the process has been found to give the compound of the formula 1 in poor yields (20%) and low purity and is, therefore, uneconomical and commercially not viable.

European Patent No 0127541 relates to the preparation of salts of amino-beta-lactamic acids by reacting the amino-beta lactamic acids with stoichiometric amount of alkyl guanidines in a solvent at −50 to +25° C. Experimental example 61 of the above European Patent relates to preparation of compound of the formula 1 by reacting potassium N-(1-ethoxycarbonyl propen-2-yl)-alpha-aminophenylacetate (Dane salt) in methylene chloride with gamma-picoline hydrochloride or pyridine or beta-picoline in the presence of N-methylacetamide followed by pivaloyl chloride. The resulting mixed anhydride is condensed with 7-ADCA in methylene chloride and tetramethylguanidine. The excess mixed anhydride was destroyed with diethyl amine. The resulting compound was hydrolysed with aqueous hydrochloric acid and treated with acetonitrile followed by cleavage of the acetonitrile solvate with water to obtain the compound of the formula 1. This process generates an acetonitrile solvate necessitating subsequent cleavage of the solvate with water. This process also uses the Dane salt in large excess (about 20% in excess of 7-ADCA) necessitating destruction of the excess Dane salt with diethyl amine. This process is, therefore, tedious and difficult to carryout. It also results in large amount of unreacted 7 ADCA in the reaction leading to poor yields and is, therefore, uneconomical.

SUMMARY

An object of the invention is to provide a process for the manufacture of the antibiotic 7-(D-α-amino-α-phenylacetamido-3-methyl-3-cephem-4-carboxylic acid (cephalexin) of the formula 1 and pharmaceutically acceptable salts thereof in high yield and purity.

Another object of the invention is to provide a process for the manufacture of the antibiotic 7-(D-α-amino-α-phenylacetamido)- 3-methyl-3-cephem-4-carboxylic acid (cephalexin) of the formula 1 and pharmaceutically acceptable salts thereof which is simple, easy and convenient to carry out.

Another object of the invention is to provide a process for the manufacture of the antibiotic 7-(D-αamino-α-phenylacetamido)-3-methyl-3-cephem-4-carboxylic acid (cephalexin) of the formula 1 and pharmaceutically acceptable salts thereof which is economical and commercially viable.

DETAILED DESCRIPTION

According to the invention there is provided a process for the manufacture of the antibiotic 7-(D-α-amino-α-phenylacetamido)-3-methyl-3-cephem-4-carboxylic acid (cephalexin) of the formula 1:

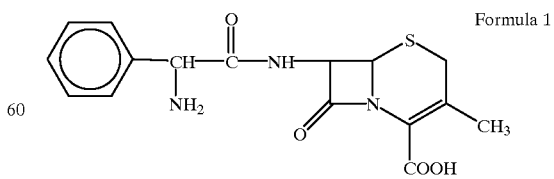

Formula 1 and pharmaceutically acceptable salts thereof consisting of reacting an enamine protected potassium salt of D-(-)-α-phenyl glycine (Dane salt) of the formula 5:

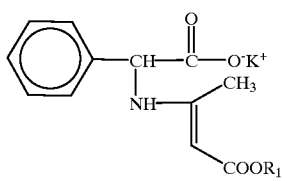

Formula 5 wherein R₁ is methyl or ethyl with an acid chloride of the formula R₂COCl, wherein R₂ is ethyl or tertiary butyl in a twin solvent mixture herein described in the ratio 6:1 to 1:1 in the presence of a pyridine derived twin catalytic mixture herein described in the ratio 1:0.01 to 1:0.05 at −20 to −65° C. to obtain a mixed anhydride of the formula 4:

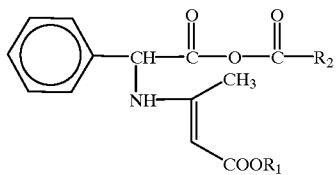

Formula 4 wherein R₁ and R₂ are ae defined above which ie condensed with an alkyl guanidinium salt solution of 7-amino desacetoxy cephalosporanic acid (7-ADCA) of the formula 2:

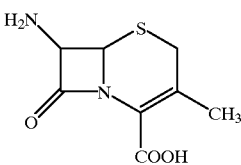

Formula 2 at −10° C. to −65° C. followed by hydrolytic cleavage of the enamine derivative of the resulting compound of the formula 6f:

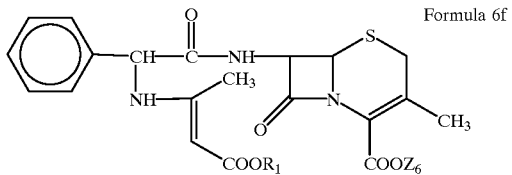

Formula 6f wherein R₁ is as defined above and Z₆ is alkyl guanidinium with an aqueous mineral acid herein described and precipitation of the compound of the formula 1 with a base herein described in the presence of an alcohol as co-solvent herein described and if desired converting the compound of the formula 1 into pharmaceutically acceptable salts thereof in a known manner.

The acid chloride is of the formula R₂COCl includes alkyl acyl chlorides such as methyl chloroformate, ethyl chloroformate or trimethyl acetyl chloride (pivaloyl chloride) preferably pivaloyl chloride.

The alkyl guanidinium represented by Z₆ in formula 6f is, for example, pentamethyl guanidinium or tetramethyl guanidinium.

Preferably, R₁ in formulae 4, 5 and 6f is methyl and R₂ in formula 4 is ethyl and Z₆ in formula 6f is tetramethyl guanidinium.

The twin solvent mixture comprises a halogenated hydrocarbon solvent such as methylene chloride, chloroform, ethylene dichloride or carbon tetra chloride preferably methylene chloride and a polar aprotic solvent selected from the group comprising N,N-dimethyl formamide, N,N-dimethyl acetamide or N,N-dimethyl sulfoxide, preferably N,N-dimethyl acetamide.

The halogenated hydrocarbon solvent and polar aprotic solvent are preferably in the ratio 2:1.

The pyridine derived twin catalytic mixture comprises protonated pyridine derivates and alkyl substituted pyridines. As a protonated pyridine species substituted or non-substituted pyridinium hydro halides such ae pyridinium hydrochloride/hydrobromide or β- or γ-picoline hydrochlorides/hydrobromides may be used. Preferred protonated pyridine is pyridinium hydrobromide. As alkyl substituted pyridines monoalkyl or dialkyl pyridine derivates such as β- or γ-picoline, 2,3; 2,4; 2,5 or 2,6 Lutidine may be used. Preferred alkyl substituted pyridine is 2,6 Lutidine. The compound of the formula 5 and the twin catalytic mixture are preferably in the ratio 1:0.01 to 1:0.04.

The reaction of Dane salt of the formula 5 with acid chloride is carried out preferably at −35° C.

The condensation of the mixed anhydride of the formula 4 with the alkyl guanidinium salt solution of 7-ADCA of the formula 2 is carried out preferably at −40 to −45° C.

The hydrolytic cleavage of the compound of formula 6e is carried out in the presence of an aqueous mineral acid such as hydrochloric acid or hydrobromic acid, preferably hydrochloric acid.

The base used for precipitation of the compound of the formula 1 is ammonia or an alkyl substituted ammonia such ae di or triethyl amine or di isopropylamine preferably trietlylamine.

The alcohol used for precipitation of the compound of the formula 1 is lower chain alcohol such as methanol, ethanol or n-or-iso-propanol preferably methanol.

If desired the compound of the formula 1 is converted into pharmaceutically acceptable salts thereof in known manner by treating with alkali such as sodium or potassium hydroxide.

The process of the invention does not use ester functionality, methanol in excess for dissolution of 7-ADCA, acetone for mixed anhydride formation or mixed anhydride in large excess. The twin solvent mixture ensures complete conversion of 7-ADCA into the product and eliminates emulsion formation and makes separation and purification procedures of compound of the formula 1 easy and convenient to carry out. The catalytic mixture accelerates the reaction and ensures complete conversion of the 7-ADCA into the product. Therefore, the process of the invention is simple, easy and convenient and fast to carryout and gives the compound of the formula 1 in high yields (about 82%) and in high purity (about 99%). For the above reasons the process of the invention is economical and commercially viable.

The following examples are illustrative of the invention but not limitative to the scope thereof.

EXAMPLE 1

38 g of potassium N-(1-ethoxy carbonyl-1-propen-2-yl)-D(−)-α-amino phenyl acetate was suspended in 150 ml of methylene chloride 30 minutes. To thiS 0.5 g of pyridine hydrobromide was added followed by 75 ml of N,N-dimethyl acetamide and 1.4 ml of 2,6-Lutidine. The above mixture was cooled to −40° C. and 17 ml of pivaloyl chloride was added and the reaction mass maintained at −35° to −40° C. for 1 hr. The temperature of the reaction mixture was raised to −20° C. over a period of 30 minutes and cooled rapidly to −65° C. The reaction was buffered with 1.4 ml of 2-ethyl hexanoic acid. A solution of 25 g 7-ADCA and 16 ml in 100 ml of methylene chloride was added to the reaction at −20° C. The reaction was maintained at −40 to −45° C. for 3.5 hrs and warmed to −10° C. over a period of 30 minute. 200 ml of water and 40 ml of HCl were added and the reaction mixture was stirred vigorously. After 30 minutes the upper aqueous phase was filtered and diluted with 50 ml methanol. To this triethylamine (35 ml) was added under stirring at room temperature over a period of 15 minutes to adjust the pH to 5.5. The thick white precipitated mass was slowly cooled to 0° C. and after 1 hr in crystallization filtered, washed with 25 ml ice-water followed by chilled 50% acetone-water (50 ml) and chilled acetone (50 ml). The precipitate was dried at 40° to give 35 g of cephalexin monohydrade.

Water (by Karl Fisher)=6% (Pharmacopoeial specification=4–8%).

Specific Rotation (α)D=+156° (Pharmacopoeial specification=+149–+158°).

Chemical assay by HPLC (High Pressure Liquid Chromatography)=99.11%, NLT (NOT LESS THAN)= 95%. Yield=82% (By theory on 7-ADCA) (theoretical=42.6 g).

EXAMPLE 2

The procedure of Example 1 was followed with 0.5 g of β-picoline hydrochloride instead of pyridine hydrobromide.

Water (by Karl Fisher)=6% (Pharmacopoeial specification=4–8%).

Specific Rotation (α)D=+156° (Pharmacopoeial specification=+149–+158°).

Chemical assay by HPLC=99.11%, NLT=95%. Yield= 82% (By theory on 7-ADCA) (theoretical=42.6 g).

EXAMPLE 3

The procedure of Example 1 was followed with 0.5 g of r-picoline hydrochloride instead of pyridine hydrobromide.

Water (by Karl Fisher)=6% (Pharmacopoeial specification=4–8%).

Specific Rotation (α)D=+156° (Pharmacopoeial specification=+149–+158°).

Chemical assay by HPLC=99.11%, NLT=95%. Yield= 82% (By theory on 7-ADCA) (theoretical=42.6 g).

EXAMPLE 4

The procedure of Example 1 was followed with 75 ml N,N-dimethyl formamide instead of N,N-dimethyl acetamide.

Water (by Karl Fisher)=5.8% (Pharmacopoeial specification=4–8%).

Specific Rotation (α)D=+155.5° (Pharmacopoeial specification=+149–+158°)

Chemical assay by HPLC =99%, NLT=95% Yield=82% (By theory on 7-ADCA) (theoretical=42.6 g).

EXAMPLE 5

25 gms of cephalexin monohydrate was suspended in 75 ml of water. To this under stirring, 5.75 gms of sodium bicarbonate was added. The solution were filtered and lyophilized to afford 24 gms of crystalline cephalexin sodium.

Yield=95% [By theory on cephalexin monohydrate (theoretical=25.3 g)].

We claim:

1. A process for the manufacture of the antibiotic 7-(D-α-amino-α-phenylacetamido)-3-methyl-3-cephem-4-carboxylic acid (cephalexin) of the formula 1:

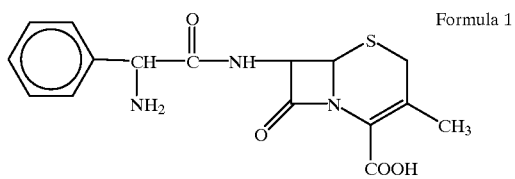

Formula 1 or a pharmaceutically acceptable salt thereof, the process comprising reacting at −20° C. to −65° C. an enamine protected potassium salt of D-(−)-α-phenyl glycine (Dane salt) of the formula 5:

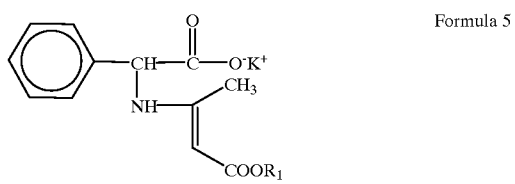

Formula 5 wherein $R_1$ is methyl or ethyl with an acid chloride of the formula $R_2COCl$, wherein $R_2$ is ethyl or tertiary butyl, in a twin solvent mixture, wherein the compound of the formula 5 and the twin catalytic mixture are in a ratio of 1:0.01 to 1:0.05, to obtain a mixed anhydride of the formula 4:

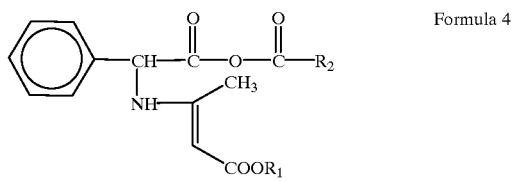

Formula 4 wherein $R_1$ and $R_2$ are as defined above, the mixed anhydride of the formula 4 being condensed at −10° C. to −65° C. with an alkyl guanidinium salt solution of 7-amino desacetoxy cephalosporanic acid (7-ADCA) of the formula 2:

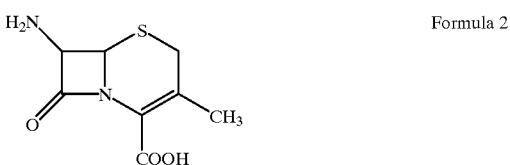

Formula 2 followed by hydrolytic cleavage with an aqueous mineral acid of the enamine derivative of the resulting compound of the formula 6f:

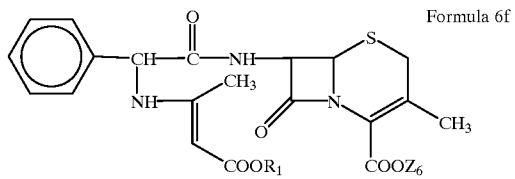

Formula 6f

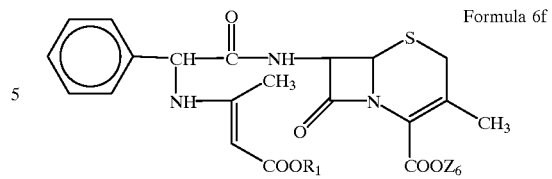

Formula 6f wherein $R_1$ is as defined above and $Z_6$ is alkyl guanidinium, and precipitation of the compound of the formula 1 with a base in the presence of an alcohol as co-solvent, and if desired converting the compound of the formula 1 into a pharmaceutically acceptable salt thereof.

2. A process as claimed in claim 1, wherein the acid chloride is pivaloyl chloride.

3. A process as claimed in claim 1, wherein $R_1$ in formulae 4, 5 and 6f is methyl and $R_2$ in formula 4 is ethyl and $Z_6$ in formula 6f is tetramethyl guanidinium.

4. A process as claimed in claim 1 wherein the twin solvent mixture comprises methylene chloride and dimethyl acetamide.

5. A process as claimed in claim 1, wherein the twin solvent mixture comprises a halogenated hydrocarbon solvent and a polar aprotic solvent selected from the group consisting of N,N-dimethyl formamide, N,N-dimethyl acetamide, and N,N-dimethyl sulfoxide.

6. A process as claimed in claim 1 wherein the twin catalytic mixture comprises pyridinium hydrobromide and 2,6 Lutidine.

7. A process as claimed in claim 1, wherein the compound of the formula 5 and the twin catalytic mixture are in a ratio of 1:0.01 to 1:0.04.

8. A process as claimed in claim 1 wherein the reaction of Dane salt of the formula 5 with acid chloride is carried out at −35° C.

9. A process as claimed in claim 1, wherein the condensation of the mixed anhydride of the formula 4 with the alkyl guanidinium salt solution of 7-ADCA of the formula 2 is carried out at −40° C. to −45° C.

10. A process as claimed in claim 1 wherein the hydrolytic cleavage of the compound of formula 6f is carried out in the presence of hydrochloric acid.

11. A process as claimed in claims 1, wherein the base used for precipitation of compound of the formula 1 is triethylamine.

12. A process as claimed in claim 1, wherein the alcohol used in the precipitation of the compound of the formula 1 is methanol.

13. A process for the manufacture of the antibiotic 7-(D-α-amino-α-phenylacetamido)-3-methyl-3-cephem-4-carboxylic acid (cephalexin) of formula 1:

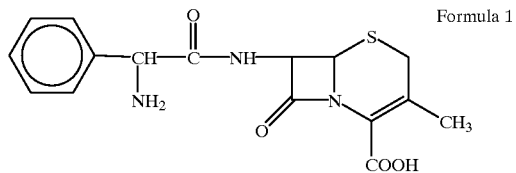

Formula 1 or a pharmaceutically acceptable salt thereof, the process comprising hydrolytic cleavage with an aqueous mineral acid of a compound of formula 6f:

wherein $R_1$ is methyl or ethyl and $Z_6$ is alkyl guanidinium, to yield an aqueous phase, precipitating from the aqueous phase the compound of formula 1 with a base in the presence of an alcohol as a co-solvent, and optionally converting the compound of formula 1 into a pharmaceutically acceptable salt thereof.

14. A process as claimed in claim 13, wherein the compound of formula 6f is prepared by condensing at −10° C. to −65° C. a mixed anhydride of formula 4:

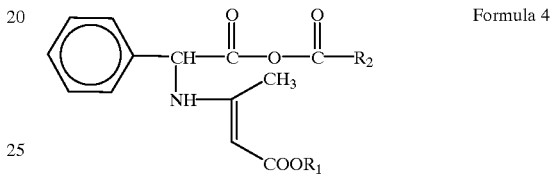

Formula 4 with an alkyl quanidinium salt solution of 7-amino desacetoxy cephalosporanic acid (7-ADCA) of formula 2:

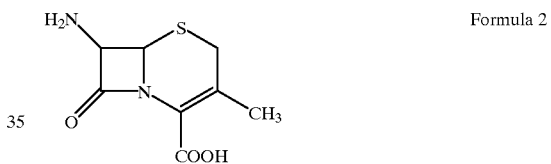

Formula 2 wherein $R_1$ is methyl or ethyl and wherein $R_2$ is ethyl or tertiary butyl.

15. A process as claimed in claim 14, wherein $Z_6$ is pentamethyl guanidinium or tetramethyl guanidinium.

16. A process as claimed in claim 5, wherein the ratio of the halogenated hydrocarbon solvent to the polar aprotic solvent ranges from 6:1 to 1:1.

17. A process as claimed in claim 5, wherein $Z_6$ is pentamethyl guanidinium or tetramethyl guanidinium; wherein the halogenated hydrocarbon solvent is selected from the group consisting of methylene chloride, chloroform, ethylene dichloride, and carbon tetrachloride; wherein the twin catalytic mixture comprises a protonated pyridine derivative and an alkyl substituted pyridine; wherein the protonated pyridine derivative is selected from the group consisting of substituted or nonsubstituted pyridinium hydrochloride, pyridinium hydrobromide, β-picoline hydrochloride, γ-picoline hydrochloride, β-picoline hydrobromide, and γ-picoline hydrobromide; wherein the alkyl substituted pyridine is selected from the group consisting of β-picoline, γ-picoline, 2,3 Lutidine, 2,4 Lutidine, 2,5 Lutidine, and 2,6 Lutidine; and wherein the acid chloride of the formula $R_2COCl$ is trimethyl acetyl chloride.

18. A process as claimed in claim 17, wherein the aqueous mineral acid is hydrochloric acid or hydrobromic acid; wherein the base used for precipitation of the compound of formula 1 is ammonia or an alkyl substituted ammonia; and wherein the alcohol used in the precipitation of the compound of the formula 1 is selected from the group consisting of methanol, ethanol, n-propanol, and isopropanol.

19. A process as claimed in claim 1, wherein the compound of the formula 1 is converted into a pharmaceutically acceptable salt thereof by treatment with an alkali.

20. A process as claimed in claim 15, wherein the aqueous mineral acid is hydrochloric acid or hydrobromic acid; wherein base used for precipitation of the compound of formula 1 is ammonia or an alkyl substituted ammonia; and wherein the alcohol used in the precipitation of the compound of formula 1 is selected from the group consisting of methanol, ethanol, n-propanol, and isopropanol.

21. A process as claimed in claim 14, wherein $R_1$ in formulae 4 and 6f is methyl, $R_2$ in formula 4 is ethyl, and $Z_6$ in formula 6f is tetramethyl guanidinium.

22. A process as claimed in claim 20, wherein $R_1$ in formulae 4 and 6f is methyl, $R_2$ in formula 4 is ethyl, and $Z_6$ in formula 6f is tetramethyl guanidinium.

* * * * *